United States Patent [19]
Adams et al.

[11] Patent Number: 5,735,866
[45] Date of Patent: Apr. 7, 1998

[54] ADJUSTABLE LENGTH SAW BLADE

[75] Inventors: Kenneth M. Adams, Tampa; Sorin Nenu, Clearwater, both of Fla.

[73] Assignee: Linvatec Corporation, Largo, Fla.

[21] Appl. No.: 715,945

[22] Filed: Sep. 19, 1996

[51] Int. Cl.⁶ .............................. A61B 17/14; B26B 1/00
[52] U.S. Cl. ........................ 606/178; 606/82; 606/176; 30/339
[58] Field of Search ............................ 606/82, 176, 177, 606/178; 30/339, 337, 342, 349, 351, 335

[56] References Cited

U.S. PATENT DOCUMENTS

| | | | |
|---|---|---|---|
| 4,386,609 | 6/1983 | Mongeon | 30/339 |
| 4,461,296 | 7/1984 | Hodge | 128/317 |
| 4,617,930 | 10/1986 | Saunders | 128/317 |
| 4,637,391 | 1/1987 | Schlein | 128/317 |
| 5,178,626 | 1/1993 | Pappas | 606/178 |
| 5,382,249 | 1/1995 | Fletcher | 606/79 |
| 5,439,472 | 8/1995 | Evans et al. | 30/339 |

OTHER PUBLICATIONS

Hall Oscillating Saw Blades, pp. 2, 3 –The Hall® Blade and Bur Book –Literature No. 97–3000–320, Rev. A, c1991.

*Primary Examiner*—Michael Buiz
*Assistant Examiner*—Julian W. Woo
*Attorney, Agent, or Firm*—Cary R. Reeves

[57] ABSTRACT

A saw blade has two portions that are adjustable relative to one another in order to vary the overall length of the saw blade. A hub portion includes a hub adapted to engage a saw. Opposite the hub is an engagement end. A blade portion carries cutting teeth. Opposite the teeth is an engagement end. The engagement end of the blade portion engages the engagement end of the hub portion. The engagement ends carry a releasable lock to hold them in engagement to form a saw blade of a particular length. To change the saw blade length, the lock is released, the engagement ends moved relative to one another, and the lock reengaged. A locking sleeve can be slid to enclose the engagement portions to more securely hold them in engagement.

4 Claims, 2 Drawing Sheets

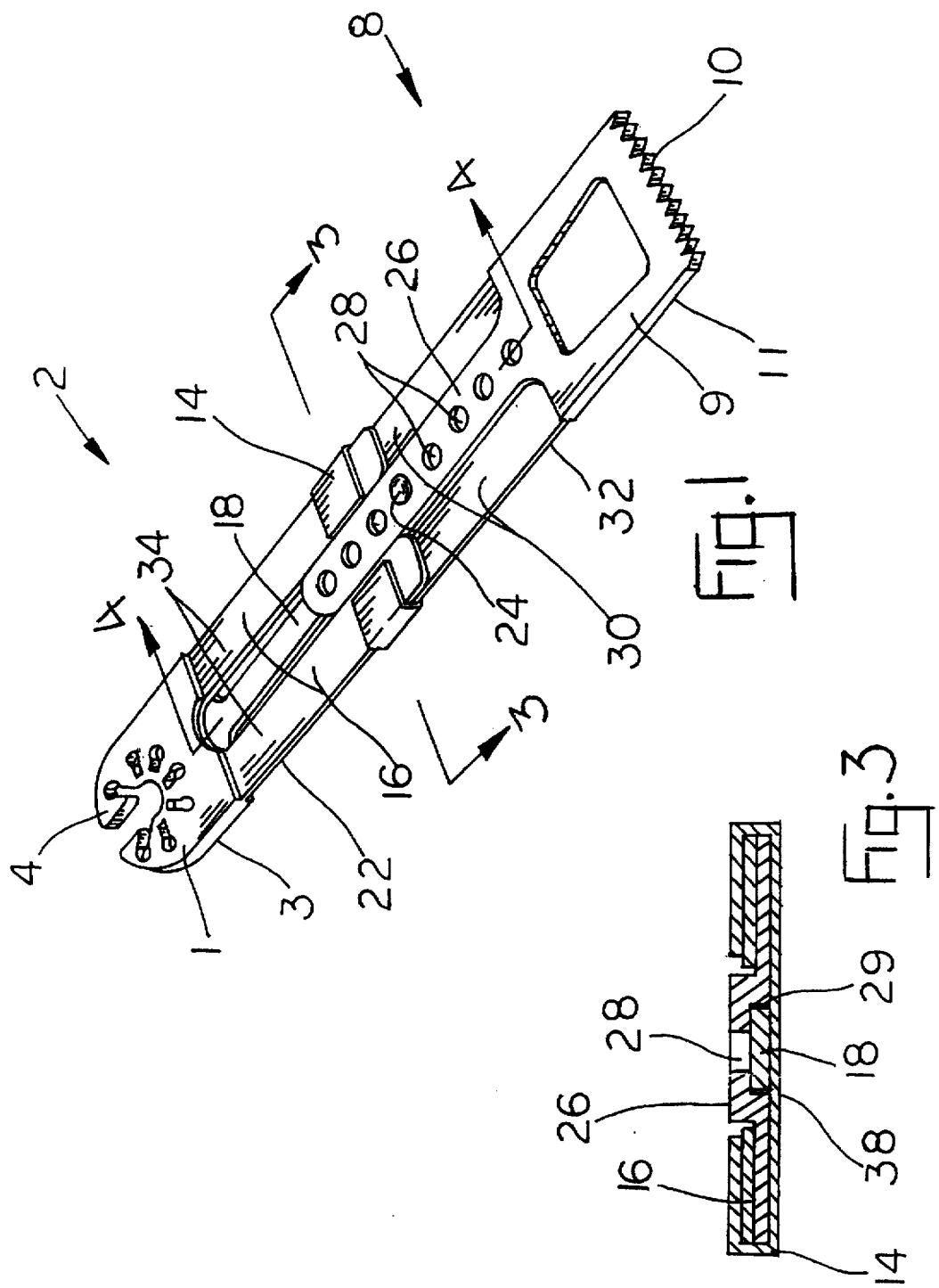

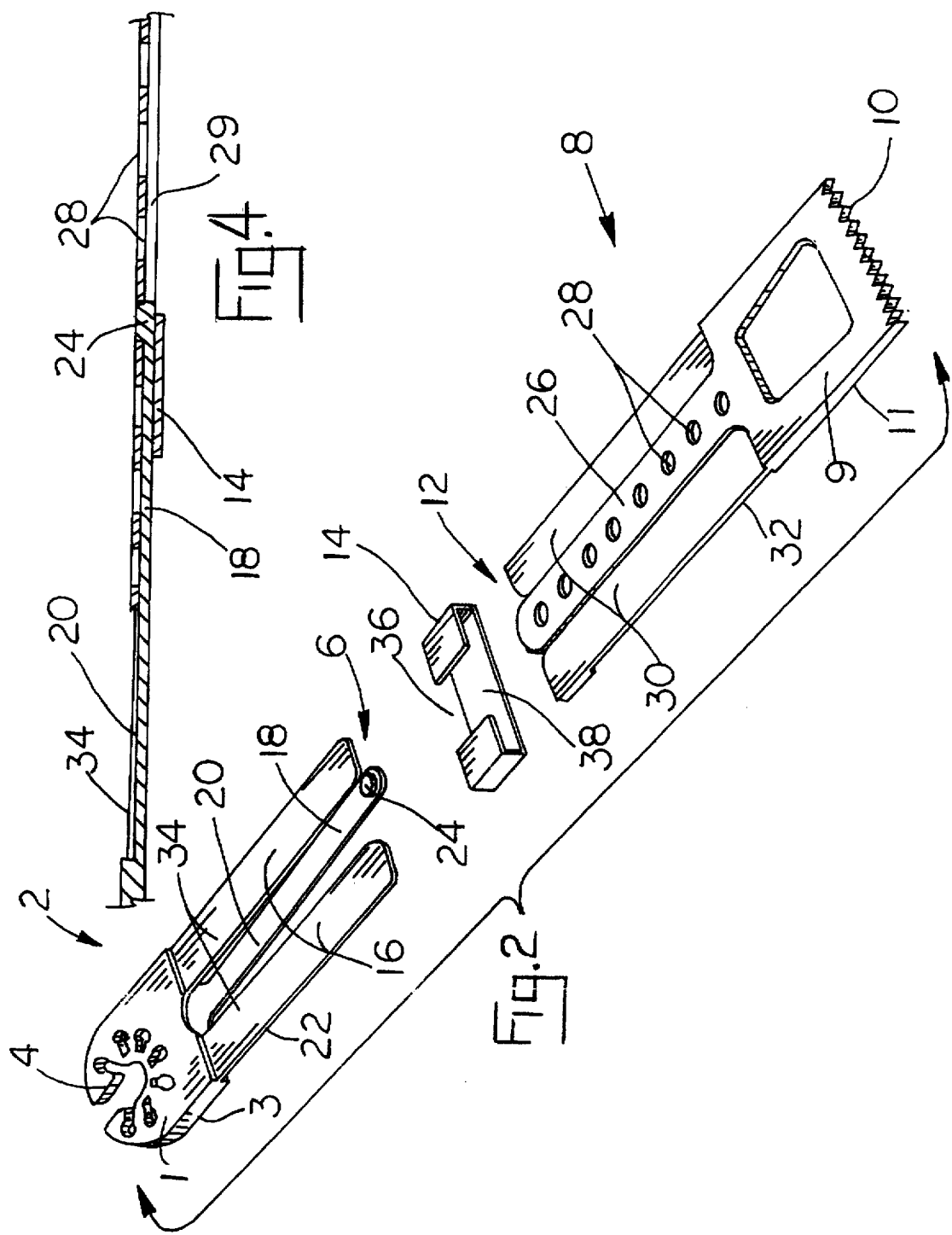

5,735,866

ADJUSTABLE LENGTH SAW BLADE

BACKGROUND OF THE INVENTION

The present invention relates to saw blades and more particularly to saw blades for orthopaedic surgery.

There are many instances when it is desirable to change the length of a saw blade. An example is a surgical operation to replace a diseased knee joint. In such an operation a saw blade, often an oscillating blade, is inserted through a plurality of slots in a cutting block to cut the end of the femur to a desired shape. It is preferred that the blade extend only slightly farther than is required to make the desired cut so that adjacent tissues are not unneccessarily cut. Since the different cutting slots often have different dimensions, it is necessary to use a different length of saw blade with each slot. Some surgeons place a piece of adhesive tape on the saw blade to indicate the amount of blade to use for a particular cut. The surgeon then must restrain the saw blade manually to prevent it from engaging the slot deeper than the depth indicated by the tape. U.S. Pat. No. 4,461,296 issued to Hodge teaches a surgical saw blade having a guard fixed a predetermined distance from the cutting edge to control the depth of cut. Similarly, U.S. Pat. No. 4,637,391 issued to Schlein teaches a surgical saw blade having a depth guard releasably secured to the blade. The position of the stop is adjustable in order to adjust the depth of the cut. U.S. Pat. No. 5,382,249 issued to Fletcher teaches another way to control the amount of saw blade used. Fletcher teaches several spaced-apart pairs of notches disposed in the blade edges. Each pair of notches is adapted to engage a pair of pins in the power tool. The mount of blade extending beyond the tool is adjustable by changing the position of the blade within the tool.

SUMMARY OF THE INVENTION

The present invention provides a surgical saw blade having two portions that are adjustable relative to one another in order to vary the overall length of the saw blade. A hub portion includes a hub adapted to engage a saw. Opposite the hub is an engagement end. A blade portion carries cutting teeth. Opposite the teeth is an engagement end. The engagement end of the blade portion engages the engagement end of the hub portion. The engagement ends carry a releasable lock to hold them in engagement to form a saw blade of a particular length. To change the saw blade length, the lock is released, the engagement ends moved relative to one another, and the lock reengaged. A locking sleeve can be slid to enclose the engagement portions to more securely hold them in engagement. In addition to allowing the blade length to be adjusted, the present invention allows the cutting portion to be changed while leaving the hub portion attached to the saw. This is useful when it is desired to change a dulled cutting portion or to change to a different size or style cutting portion. Economy can be realized in manufacturing and inventory if the hub portion is reusable and only the blade portion is disposable. One standard blade portion cart be made and put into inventory that can be used with the hub portion to provide many different overall blade lengths.

BRIEF DESCRIPTION OF THE DRAWINGS

FIG. 1 is a perspective view of an assembled blade according to the present invention.

FIG. 2 is a perspective exploded view of the blade of FIG. 1.

FIG. 3 is a section view of the blade of FIG. 1 taken along line 3–3.

FIG. 4 is a section view of the blade of FIG. 1 taken along line 4–4.

DETAILED DESCRIPTION OF THE INVENTION

FIGS. 1–4 depict an exemplary oscillating surgical saw blade according to the present invention. A hub portion 2 comprises an elongated flat plate having top 1 and bottom 3 sides. A hub 4 is formed at one end. The hub 4 is adapted for engagement with a power tool. In the example shown, the hub 4 includes a plurality of radially oriented holes and slots for engaging pins on the power tool. An engagement end 6 is formed at the other end opposite the hub 4. A blade portion 8 comprises an elongated flat plate having top 9 and bottom 11 sides. Teeth 10 are formed at a cutting end. The teeth 10 are adapted for cutting bone or other materials. An engagement end 12 is formed at the other end opposite the teeth 10. The engagement ends 6 and 12 fit together to form a saw blade having both a hub 4 and teeth 10. The engagement ends 6 and 12 carry a releasable fastener to hold them in engagement to form a saw blade of a particular length. To change the saw blade length, the lock is released, the engagement ends 6 and 12 are moved relative to one another, and the lock reengaged. An optional locking sleeve 14 can be slid to enclose the engagement ends 6 and 12 to more securely hold them in engagement.

In the embodiment shown, the releasable fastener includes a tongue and groove arrangement that is secured with a button in a hole. The engagement end 6 of the hub portion 2 includes two cantilevered side arms 16 and a cantilevered central arm 18. Preferably the arms 16 and 18 are formed by milling them from the flat plate of the hub portion 2. The arms 16 and 18 are attached to the hub portion 2 near the hub 4 and project away from the hub 4. The top of the central arm 18 is milled below the top side 1 of the hub portion to form a relieved top surface 20. The bottoms of the side arms 16 are milled above the bottom side 2 of the hub portion 2 to form relieved lower surfaces 22. The end of the central arm 18 away from the hub 4 carries a button 24. The central arm 18 is bent so that it is biased upwardly between the side arms 16.

The engagement end of the blade portion includes a central web 26 extending between the end containing the teeth 10 and the engagement end 12. A series of through holes 28 is formed in the central web 26 along its length. A groove 29 is formed in the bottom of the central web 26 by milling above the bottom side 11 along the length of the central web 26. Adjacent to each side of the central web 26, running along the length of the central web 26, are two relieved lateral surfaces 30 formed by milling below the top side 9 of the blade portion 8.

Preferably material is removed across the bottom side 11 of the blade portion 8, opposite the lateral surfaces 30, to provide a blade portion locking sleeve relief 32. The blade portion locking sleeve relief 32 provides a recess for the locking sleeve 14 so that it does not project below the bottom side 11. Similarly, material is preferably removed from the tops of the side arms 16 to provide a hub portion locking sleeve relief 34. The optional locking sleeve 14 comprises a channel sized to slip onto the blade portion 8. Preferably the locking sleeve 14 is a C-shaped channel made from thin metal sheet stock having an open side 36 and a closed side 38. The open side 36 of the locking sleeve 14 is adapted to straddle the central web 26.

To assemble the saw blade, the central arm 18 is flexed downwardly so that it is parallel to the side arms 16. The engagement ends 6 and 12 are brought together so that the side arms 16 slide along the lateral surfaces 30 and the central arm 18 slides in the groove 29. The bias of the central arm 18 causes it to press into the groove 29. When the button 24 aligns with a hole 28 it will snap into the hole 28 and prevent the hub portion 2 and blade portion 8 from moving relative to one another. The blade fits together with an overall thickness no greater than the thickness of the hub 4, since the lateral surfaces 30 and groove 29 are relieved on sides opposite to the sides that the side arms 16 and central arms 18 are relieved on. To adjust the blade's length, the central arm 18 is flexed downwardly away from the groove 29 in order to remove the button 24 from the hole 28. The central arm 18 can be flexed by pressing; directly on the central arm 18 or by flexing the teeth 10 and hub 4 upwardly causing the blade to bow and the free end of the central web 26 to press against the central arm 18 and flex it back. The hub and blade portions 2 and 8 are repositioned relative to one another to the desired overall blade length and the central arm 18 is released so that the button 24 can secure the portions.

To use the optional locking sleeve 14, it is slipped onto the blade portion 8 prior to combining the two engagement ends 6 and 12. The engagement ends 6 and 12 are then assembled as described above. To lock the engagement ends 6 and 12 and prevent the button 24 from disengaging from the hole 28, the locking sleeve is slid to enclose the overlapping portions of the engagement ends 6 and 12. The closed side 38 of the locking sleeve 14 lies in the blade portion locking sleeve relief 32 and the open side 36 ends of the locking sleeve 14 lie in the hub side locking sleeve relief 34 so that the locking sleeve 14 does not project beyond the top or bottom sides 1 and 2.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A saw blade having a longitudinal axis, the saw blade comprising; a hub portion, a blade portion engaging the hub portion, the blade portion including a cutting end, and a locking mechanism carried by the hub and blade portions, the locking mechanism releasably preventing relative motion between the hub and blade portions, the hub and blade portions being configured to be assembled and locked in a first position in which the hub and cutting end are spaced a first distance along the longitudinal axis, and the hub and blade portions being configured to be assembled in a second position in which the hub and cutting end are spaced a second distance along the longitudinal axis, wherein the hub portion includes a hub end and an engagement end and the blade portion includes a cutting end and an engagement end, the engagement ends of the hub and blade portions being slidingly engageable to guide the hub and blade portions in relative sliding motion along the longitudinal axis, the locking mechanism being operable between a first position in which it prevents relative motion between the hub and blade portions along the longitudinal axis and a second position in which it allows relative motion between the hub and blade portions along the longitudinal axis, further wherein the engagement ends of the hub and blade portions are engageable in a tongue-and-groove fashion, the hub portion having a pair of side arms extending from the hub parallel to the longitudinal axis and a central arm extending from the hub parallel to the longitudinal axis between the side arms, the blade portion having a pair of lateral surfaces extending from the cutting end parallel to the longitudinal axis, the lateral surfaces being joined along their length by a central web, the hub and blade portions engaging one another with the side arms lying on top of the lateral surfaces and the central arm lying below the central web.

2. The saw blade of claim 1 wherein the central web includes a plurality of holes spaced along its length and the central arm carries a button, the central arm being biased toward the central web, the button being adapted to fit within each of the holes.

3. The saw blade of claim 2 further comprising a locking sleeve, the locking sleeve slightingly engaging the blade, the locking sleeve being movable from a first position in which it prevents the central arm from moving away from the central web to a second position in which it does not prevent the central arm from moving away from the central web.

4. A saw blade having a longitudinal axis, a first end, a second end, and a length as measured from the first end to the second end, the saw blade comprising two separate portions joined together and releasably locked by a locking mechanism to prevent relative motion along the longitudinal axis of the first end relative to the second end, the locking mechanism being operable to allow relative motion between the hub and blade portions along the longitudinal axis so that the length of the saw blade may be adjusted.

* * * * *